(12) United States Patent
Heeren

(10) Patent No.: US 11,547,604 B2
(45) Date of Patent: Jan. 10, 2023

(54) METHOD AND APPARATUS FOR PERFORMING OPHTHALMIC PROCEDURES REMOVING UNDESIRABLE FEATURES USING LASER ENERGY

(71) Applicant: NOVARTIS AG, Basel (CH)

(72) Inventor: Tammo Heeren, Aliso Viejo, CA (US)

(73) Assignee: Alcon Inc., Fribourg (CH)

( * ) Notice: Subject to any disclaimer, the term of this patent is extended or adjusted under 35 U.S.C. 154(b) by 477 days.

(21) Appl. No.: 16/668,353

(22) Filed: Oct. 30, 2019

(65) Prior Publication Data

US 2020/0060873 A1 Feb. 27, 2020

Related U.S. Application Data

(62) Division of application No. 15/225,146, filed on Aug. 1, 2016, now Pat. No. 10,492,951.

(51) Int. Cl.
| | |
|---|---|
| *A61F 9/008* | (2006.01) |
| *A61B 3/10* | (2006.01) |
| *A61B 3/00* | (2006.01) |
| *G16H 10/60* | (2018.01) |
| *G16H 30/40* | (2018.01) |
| *G16H 40/63* | (2018.01) |
| *G16H 20/30* | (2018.01) |
| *A61B 34/20* | (2016.01) |
| *A61B 90/00* | (2016.01) |

(52) U.S. Cl.
CPC ............ *A61F 9/008* (2013.01); *A61B 3/0025* (2013.01); *A61B 3/102* (2013.01); *A61F 9/00821* (2013.01); *G16H 10/60* (2018.01); *G16H 20/30* (2018.01); *G16H 30/40* (2018.01); *G16H 40/63* (2018.01); *A61B 90/361* (2016.02); *A61B 2034/2065* (2016.02); *A61F 2009/0087* (2013.01); *A61F 2009/00844* (2013.01); *A61F 2009/00863* (2013.01); *A61F 2009/00874* (2013.01); *A61F 2009/00897* (2013.01)

(58) Field of Classification Search
CPC ..................... A61F 2009/00874; A61F 9/008
USPC ........................................................ 606/4, 6
See application file for complete search history.

(56) References Cited

U.S. PATENT DOCUMENTS

| | | | |
|---|---|---|---|
| 2011/0077557 A1* | 3/2011 | Wing ................... | A61B 8/546 601/2 |
| 2014/0257257 A1* | 9/2014 | Grant ................ | A61F 9/00825 606/4 |
| 2015/0342782 A1* | 12/2015 | Mordaunt .......... | A61F 9/00825 606/4 |

(Continued)

*Primary Examiner* — John R Downey

(57) ABSTRACT

A method and system perform an ophthalmic procedure on an eye having an optical path from the lens to the retina. An image of at least part of the eye is received in a data processing unit. The image includes the optical path. The data processing unit determines keep out zone(s) and identifies undesirable feature(s) based on the image. The keep out zone(s) include the retina. The data processing unit also selects one of the undesirable feature(s) for removal. At least part of the undesirable feature is outside of the keep out zone(s). Confirmation for removal of the undesirable feature is received in the data processing unit. In response to receiving the confirmation, a control unit controls a laser to perform laser removal the at least the portion of the undesirable feature without targeting any portion of the keep out zone(s).

14 Claims, 6 Drawing Sheets

(56) References Cited

U.S. PATENT DOCUMENTS

2016/0074214 A1* 3/2016 Palanker ............... A61F 9/0084
  606/6
2017/0326003 A1* 11/2017 Schuele .............. A61F 9/00825

* cited by examiner

METHOD AND APPARATUS FOR PERFORMING OPHTHALMIC PROCEDURES REMOVING UNDESIRABLE FEATURES USING LASER ENERGY

This application is a divisional application of U.S. Non-Provisional patent application Ser. No. 15/225,146 titled "METHOD AND APPARATUS FOR PERFORMING OPHTHALMIC PROCEDURES REMOVING UNDESIRABLE FEATURES USING LASER ENERGY," filed on Aug. 1, 2016, whose inventor is Tammo Heeren, which is hereby incorporated by reference in its entirety as though fully and completely set forth herein.

FIELD

This present disclosure relates generally ophthalmic surgery and, more particularly, to a method and apparatus for performing ophthalmic procedures removing undesirable features using laser energy.

BACKGROUND

The human eye sees by transmitting and refracting light through a clear outer portion of the eye called the cornea, transmitting the light through an aperture in the iris known as the pupil, focusing the light via a lens, transmitting the focused light through the vitreal cavity and onto the retina. The quality of the focused image depends on many factors including but not limited to the size, shape and length of the eye, the quality of the vitreous humor, and the shape and transparency of the cornea and lens. Trauma, age, disease and/or another malady may cause an individual's vision to degrade.

For example, undesirable features within the vitreal cavity may adversely vision. Vitreous opacities, otherwise known as vitreous floaters, are one type of undesirable feature. Vitreous opacities are free to move within the vitreous humor of the vitreal cavity. When sufficiently large and/or dense and within the optical path between the pupil and the retina, such vitreous opacities may obscure an individual's vision. One remedy for vitreous opacities is removal. In some cases, a small gauge vitrectomy may be performed. The small gauge vitrectomy may be performed by inserting a narrow gauge line into the vitreal cavity and removing a portion of the vitreous humor containing the vitreous opacity. Alternatively, the vitreous opacity may be removed via the application of laser energy. In such a method, a physician uses a slit lamp to view the posterior portion of the eye and localize the vitreous opacities. The physician then manually aims and fires the laser. The laser energy vaporizes at least part of a vitreous opacity. This procedure is repeated until the vitreous opacity is removed. The entire procedure is repeated for each vitreous opacity, until the vitreal fluid is deemed sufficiently clear.

Although the vitreous floaters may be removed, there are drawbacks. Small gauge vitrectomies are invasive, require an operating visit and carry the attendant risks. The use of laser energy is non-invasive and avoids these drawbacks. However, aiming of the laser may be difficult. Because the physician views the vitreal cavity along the optical path, it may be difficult to determine the depth of the location of the retina, the vitreous opacity or other relevant features. Consequently, there is a danger of missing the vitreous opacity and/or injuring the eye. Application of laser energy may also result in movement of the vitreous opacities. Thus, the physician re-aims the laser after each application of laser energy. This may consume a large amount of time. Therefore, the use of laser energy may involve multiple outpatient visits, each of which may be hours long. Such a procedure is burdensome on the patient and the physician.

Accordingly, what is needed is a mechanism for improving the removal of undesirable features in the vitreal cavity.

BRIEF SUMMARY OF THE INVENTION

A method and system perform an ophthalmic procedure on an eye having an optical path from the lens to the retina. An image of at least part of the eye is received in a data processing unit. The image includes the optical path. The data processing unit determines keep out zone(s) and identifies undesirable feature(s) based on the image. The keep out zone(s) include the retina. The data processing unit also selects one of the undesirable feature(s) for removal. At least part of the undesirable feature is outside of the keep out zone(s). Confirmation for removal of the undesirable feature is received in the data processing unit. In response to receiving the confirmation, a control unit controls a laser to perform laser removal the at least the portion of the undesirable feature without targeting any portion of the keep out zone(s).

According to the method and system disclosed herein, a physician may be better and more easily able to remove undesirable features such as vitreous opacities without surgery.

BRIEF DESCRIPTION OF SEVERAL VIEWS OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION OF THE PREFERRED EMBODIMENTS

Figure 1:
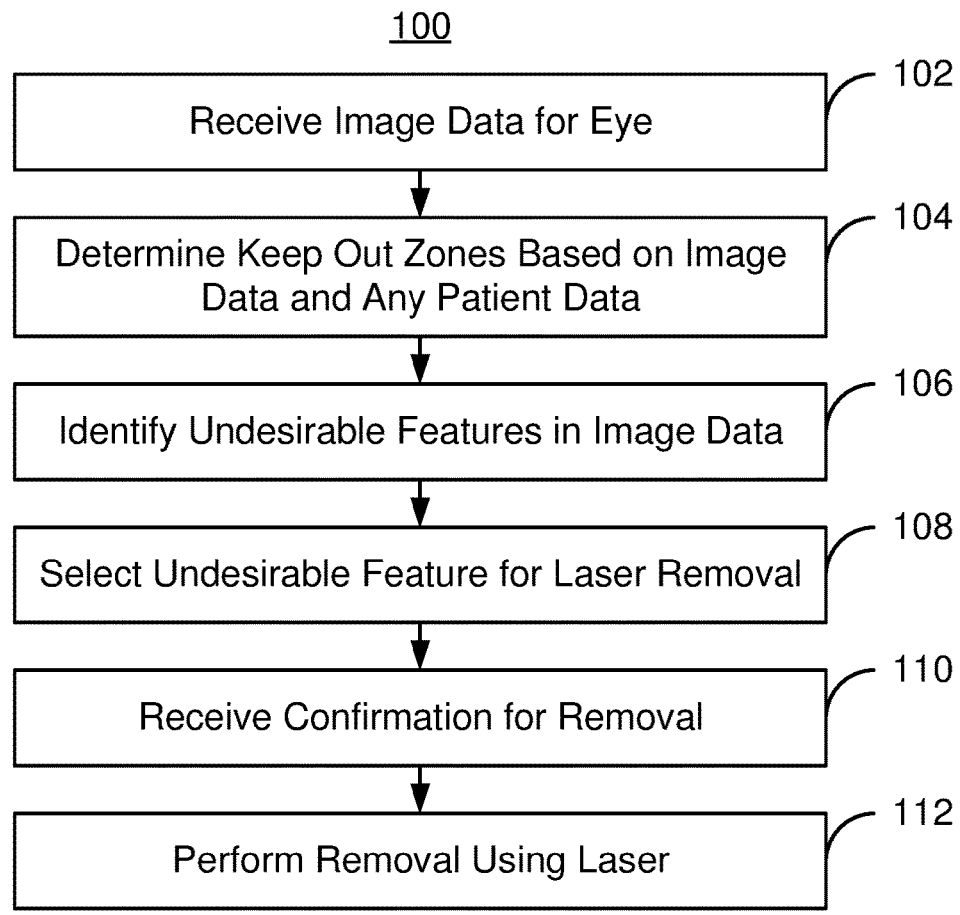
FIG. 1 is a flow chart depicting an exemplary embodiment of a method for performing an ophthalmic procedure that removes undesirable features using laser energy.

The exemplary embodiments relate to mechanisms for removing undesirable features in the vitreal cavity, such as vitreous floaters. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. Further, although specific blocks are depicted, various functions of the blocks may be separated into different blocks or combined. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

The method and system are also described in terms of singular items rather than plural items. One of ordinary skill in the art will recognize that these singular terms encompass plural. For example, an image may include one or more images. In certain embodiments, the system includes one or more processors and a memory. The one or more processors may be configured to execute instructions stored in the memory to cause and control the process set forth in the drawings and described below. As used herein, a processor may include one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality. Further, aspects of the method and system may take the form of an entirely hardware embodiment, an entirely software embodiment (including firmware, resident software, micro-code, etc.) or an embodiment combining software and hardware aspects. Furthermore, aspects of the method and system may take the form of a software component(s) executed on at least one processor and which may be embodied in one or more computer readable medium(s) having computer readable program code embodied thereon.

A method and system perform an ophthalmic procedure on an eye having an optical path from the lens to the retina. An image of at least part of the eye is received in a data processing unit. The image includes the optical path. The data processing unit determines keep out zone(s) and identifies undesirable feature(s) based on the image. The keep out zone(s) include the retina. The data processing unit also selects one of the undesirable feature(s) for removal. At least part of the undesirable feature is outside of the keep out zone(s). Confirmation for removal of the undesirable feature is received in the data processing unit. In response to receiving the confirmation, a control unit controls a laser to perform laser removal the at least the portion of the undesirable feature without targeting any portion of the keep out zone(s).

FIG. 1 is a flow chart depicting an exemplary embodiment of a method 100 for performing an ophthalmic procedure that removes undesirable features within the vitreal cavity of the eye. For simplicity, some steps may be omitted, interleaved, performed in another order and/or combined. The method 100 may include executing instructions on one or more processors. Further, the method 100 is described in the context of a non-invasive procedure. However, the method 100 may be extended to invasive procedures including but not limited to use in connection with ophthalmic surgery. The method 100 is performed by an ophthalmic laser apparatus including a data processing unit and a controller.

At least one image of at least a portion of the eye is received in the data processing unit, via step 102. Receipt of the image(s) in step 102 may include receiving image data from a separate imaging system or capturing the image by a portion of the system carrying out the method 100. Step 102 need not include rendering the image for the physician. Instead, step 102 includes obtaining data for the eye. The image(s) include the optical path of the eye. In some embodiments, the image(s) may be two-dimensional. In other embodiments, three-dimensional image(s), such as optical coherence tomograph(s) (OCTs), may be used. Thus, the image(s) may include the volume of the eye or simply a cross-section of the eye. In some embodiments, video or other mechanism for showing the progression of time may be part of the image(s) received in step 102.

Keep out zones are determined by the data processing unit based on the image data, via step 104. A keep out zone is a region of the eye in which the laser is desired not to be aimed. The keep out zones assist in ensuring that more delicate regions of the eye are not heated by the laser and, therefore, remain undamaged. Keep out zones include, for example, the retina. Step 104 may include using other patient data in addition to the image data to determine the keep out zone. For example, if the size of the patient's eye is already known, this information may be used in step 104. Step 104 may thus include identifying structures and setting a keep out zone to be the structure and a region within a particular distance of the structure. Thus, step 104 may include identifying the location of the retina from the image and/or other data and setting the keep out zone to include the retina and the region within two millimeters of the retina. In some embodiments, the keep out zone may include the retina and the region within only one millimeter of the retina. Other distances and/or other structures may be included in other keep out zones.

The physician may be allowed to adjust the size and/or location of the keep out zone as part of step 104. For example, the keep out zone corresponding to the retina that is determined by the data processing unit may include retina and the region within 0.5 millimeters of the retina. The physician may be allowed to reduced or increase the size of the keep out zone. Thus, the physician may be able to set the keep out zone for the retina as including the retina and the region within 0.25 millimeter of the retina. The physician may also be allowed to move the keep out zone to include a different part of the retina. However, there may also be a minimum distance beyond which the physician is not allowed to change the size or position of the keep out zone. In the example above, the physician may be prevented from shrinking the keep out zone such that the keep out zone is smaller than the retina.

The undesirable features within the vitreal cavity are identified by the data processing unit based on the image data, via step 106. Step 106 includes identifying a set of locations corresponding to the undesirable features. In some embodiments, only those undesirable features which intersect the optical path are detected in step 106. In other embodiments, all undesirable features that can be found based on the image data are identified. For example, vitreous floaters, or vitreous opacities, may be identified in step 106.

As used herein, a vitreous floater is synonymous with a vitreous opacity. A vitreous opacity may be any feature within the vitreous humor that has an opacity greater than a threshold and a size greater than a size threshold. Default thresholds may be provided, but may be adjusted by the user. In some embodiments, the threshold may be as low as zero. In such embodiments, any deviation from a background opacity and/or having any size may be identified as an undesirable feature. As part of step 106, the undesirable features may also be ranked based on certain characteristics. For example, the size, location, density and/or shape of the vitreous opacity may be used to rank the vitreous opacities. These characteristics may have the same weight or different weights. In some embodiments, size is given a greater weight than location and location is given a greater weight than density. Opacities that are larger, are closer to or have a larger section within the optical path and/or are more dense/more opaque may have a higher rank. As used herein, a higher ranked vitreous opacity is a vitreous opacity is more desired to be removed.

One of the undesirable features is selected by the data processing unit for removal, via step 108. At least part of this undesirable feature is outside of the keep out zone(s). Consequently, the undesirable feature may be removed by laser energy. In some embodiments, step 108 includes selecting the highest ranked (e.g. largest, most obstructive of the optical path and/or most dense). In embodiments in which the ranking is not performed as part of step 106, the ranking may be performed as part of step 108. Thus, the undesirable features may be set for removal in order from most desired to be removed to least important for removal.

A confirmation for removal of the undesirable feature is received in the data processing unit, via step 110. In some embodiments, step 110 is optional. Step 110 may include querying the physician performing the procedure and receiving a response. For example, a "REMOVE" button may be provided on the display of a user interface (U/I). In response to the physician selecting and clicking on the REMOVE button, the confirmation is received in step 110. If no confirmation is received, then the method may return to step 102 or the physician may be allowed to select a different undesirable feature for removal via the U/I. Confirmation of the removal is desired to aid in ensuring the safety of the patient.

In response to receiving the confirmation, the laser is controlled by the controller to automatically perform removal of at least part of the undesirable feature, via step 112. For example, step 112 may include automatically aiming the laser at location(s) within the selected undesirable feature, turning the laser on for a particular time and then turning the laser off (i.e. firing the laser). The laser is aimed in step 112 such that the target for the focus of the laser energy is outside of the keep out zones. Heating from the laser may be most intense at this target. Step 112 may also include setting the laser power and/or time based on the location targeted. For example, if the region at which the laser is aimed is near a keep out zone, a lower energy or shorter application of laser energy might be used. Consequently, even if there is some heating of the keep out zone, it will be relatively small.

Performing the laser removal in step 112 may include further substeps. For example, if the undesirable feature is sufficiently large and/or near the keep out zone, then multiple applications of laser energy might be required for removal. Further, the undesirable feature may not only change shape, but also move as portions of the undesirable feature are vaporized. Step 112 may then include re-imaging the eye, tracking the undesirable feature and reapplying the laser energy. Tracking the undesirable feature may include comparing the image(s) of the eye taken after the laser energy is applied with those taken before the laser energy is applied and matching the identified undesirable features identified in the later image(s) with those in the previous image(s) based on size, location, shape, and/or other criteria. These processes may be performed by the data processing unit of the ophthalmic laser apparatus. The undesirable feature selected in step 108 is tracked by the ophthalmic laser apparatus so that the laser energy tends to be applied to the same undesirable feature throughout step 112. Thus, steps 102 through 106 may be repeated as part of step 112. This process continues until the undesirable feature is considered to be removed (untrackable or missing). Some or all of the method 100 may optionally be repeated to remove the remaining undesirable features.

Using the method 100, a physician may be able to more quickly and easily remove undesirable features such as vitreous floaters, from the eye. Instead of viewing the eye, manually aiming the laser and turning the laser on or off, the physician may simply confirm removal. Because the imaging and laser removal may be performed automatically, the time taken to remove each floater may be greatly reduced. Consequently, the burden on both the physician and patient may be diminished. Because keep out zones may be automatically determined and respected by the laser removal process, the method 100 may be safer for the patient. Further, the method 100 may be performed non-invasively. Consequently, the removal of undesirable features via a laser may be improved.

Figure 2:
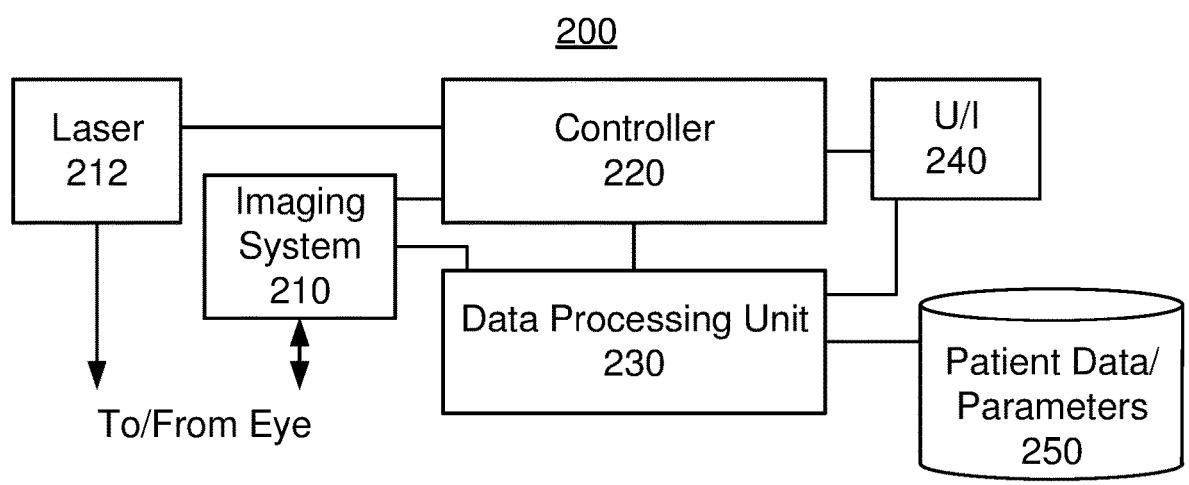
FIG. 2 is a block diagram of an exemplary embodiment of an ophthalmic laser apparatus for removing undesirable features from the vitreal cavity using laser energy.

FIG. 2 is a block diagram of an exemplary embodiment of an ophthalmic laser apparatus 200 for assisting a physician removing undesirable features from the vitreal cavity. The ophthalmic laser apparatus 200 includes an imaging system 210, laser 212, a controller 220, a data processing unit 230, a user interface (U/I) 240 and a data store 250 including any patient data, parameters and other information. For simplicity, only some components are shown. In addition, the components depicted in FIG. 2 may be packaged together in a single apparatus. Alternatively, certain components, such as portions of imaging system, laser and data processing, may be implemented separately. Further, the components may be implemented in hardware and/or software. Also shown in FIG. 2 is the sample eye 202 to be interrogated. The method 100 may be implemented using the system 200.

The imaging system 210 may include a camera and/or other image capture device that may be managed using the controller 220. In some embodiments, step 102 may include the controller 220 managing the focusing and capture of the image(s) by the imaging system 210. The camera may or may not include a microscope or other magnification that allows for enhanced detail. In other embodiments, other components may be used in for the imaging system 210. Such imaging systems 210 may or may not provide three-dimensional data for the eye. In some embodiments, video camera(s) or other mechanism for showing the progression of time may be part of the image(s) received in step 102. Further, the resolution of the imaging system 210 is sufficiently to allow the relevant features of the eye to be determined.

The laser 212 is used to vaporize portions of the undesirable features. For example, the laser 212 may be a YAG laser. The U/I 240 allows output to be provided to the physician and input to be received from the physician. For example, the physician may indicate confirmation in step 110 of the undesirable feature selected for removal via the U/I 240. The U/I 240 provides this confirmation to the data processing unit 230. The U/I 240 may also include a display for rendering image(s) of the eye or providing other visual feedback to the physician.

The data processing unit 230 receives image data from the imaging system 210 in step 102. The data processing unit 230 also performs steps 104, 106, 108 and 110. In some embodiments, the data processing unit 230 also accesses the data store 250 in order to process the image data provided in step 102.

The controller 220 communicates with the laser 212, imaging system 2120 and data processing unit 230 and user interface 240. The controller 220 manages the laser 212 and imaging system 210. For example, the control 220 may focus the camera or other image capture device in the imaging system 210, control capture of the image(s), aim the laser 212 and turn the laser 212 on/off. Using the ophthalmic laser apparatus 200, therefore, the method 100 may be implemented. One or more of the benefits of the method 100 may thus be achieved.

Figure 3:
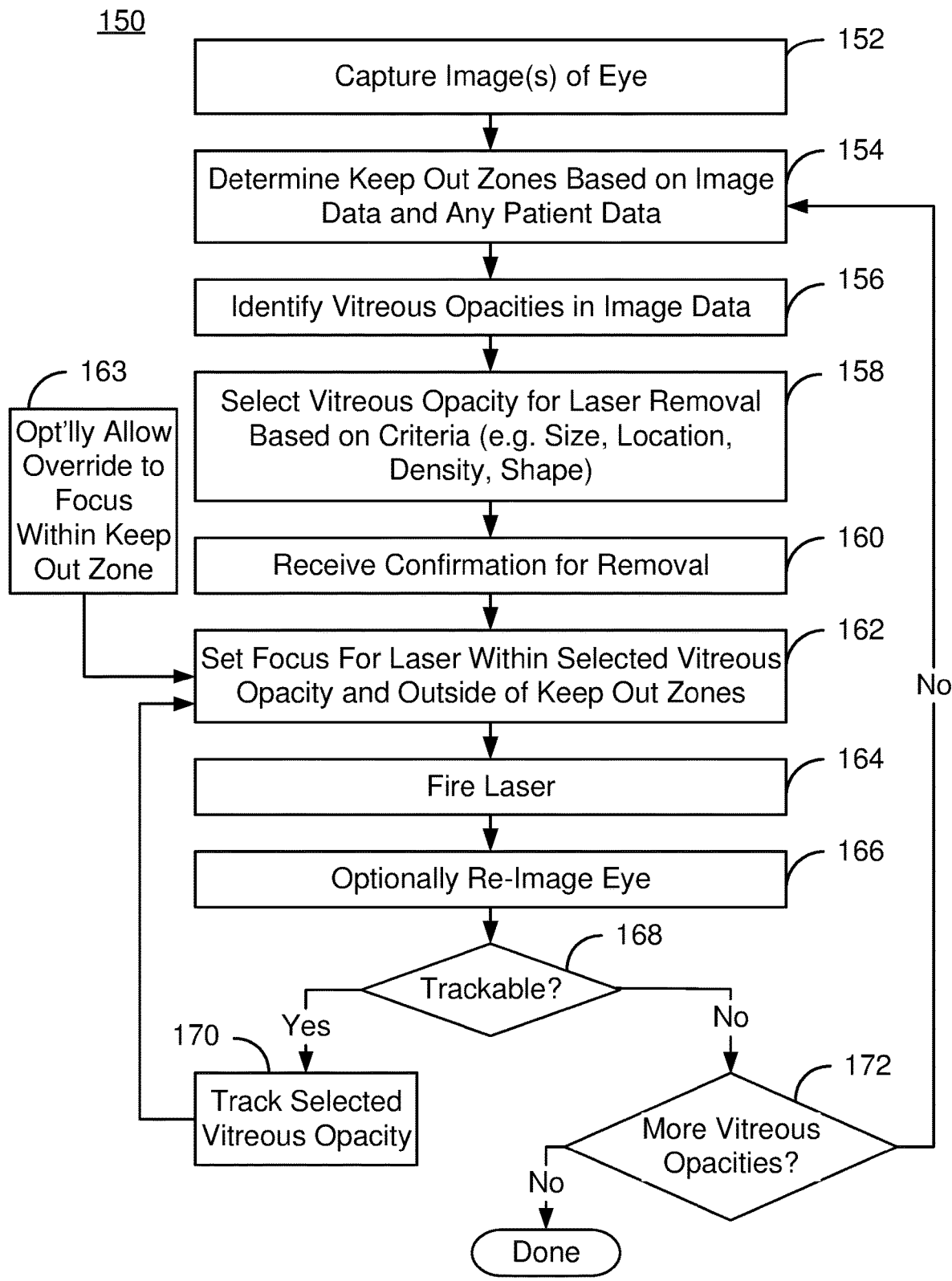
FIG. 3 is a flow chart depicting an exemplary embodiment of a method for performing an ophthalmic procedure removing undesirable features such as vitreous opacities using laser energy.

FIG. 3 is a flow chart depicting an exemplary embodiment of a method 150 for performing an ophthalmic procedure that removes undesirable features. For simplicity, the method 150 is described in the context of removal of vitreous opacities, or floaters. Some steps may be omitted, interleaved, performed in another order and/or combined. The method 150 may include executing instructions on one or more processors. Further, the method 150 is described as being performed by the system 200. However, the method 150 may be performed by other apparatuses (not shown). The method 150 may be performed non-invasively. In other embodiments, the method 150 may be incorporated in to an ophthalmic surgical procedure.

FIGS. 4A-4L depict exemplary embodiments of images/image data 300 of the eye during the method 150. FIGS. 4A-4L are not to scale. The images 300 may or may not be rendered and shown to the physician via the U/I 240. A particular patient, condition or response is not intended to be shown in FIGS. 4A-4L. In addition, the images actually captured using the method 150 may not correspond to the orientation shown. For example, images captured by a camera pointed into the pupil 308 may capture a view orthogonal to that shown in FIGS. 4A-4L. Images captured by an OCT indicate the volume of the eye. Thus, such OCT images include but are not limited to the views shown in FIGS. 4A-4L. FIGS. 4A-4L are, therefore, for explanatory purposes only and not intended to represent a specific image.

Figure 4A:
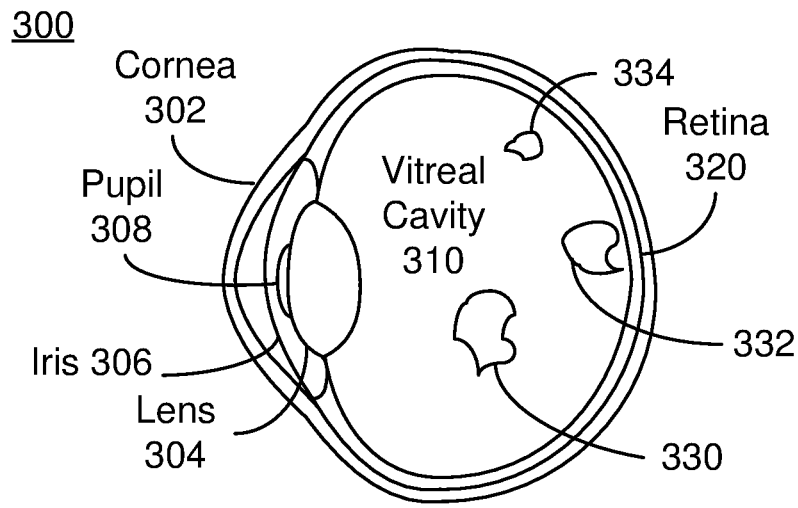
FIGS. 4A-4L depict exemplary embodiments of images of the eye during non-surgical removal of undesirable features such as vitreous opacities.

Image(s) of at least a portion of the eye are captured, via step 152. Step 152 may include the controller 220 managing the imaging system 210 to capture the image. As part of step 152, the image data for the image(s) are received by the data processing unit 230. Thus, at least part of step 152 is analogous to step 102. The image capture and image data may be for two dimensional or three dimensional views of the eye. FIG. 4A depicts an image 300 of the eye that could be considered captured in step 152. The cornea 302, lens 304, iris 306, pupil 308, vitreal cavity 310 and retina 320 are indicated for the purposes of explanation. Also shown are vitreous opacities 330, 332 and 334. Although the entire eye is shown in FIG. 4A, in other embodiments, the images capture data for only a portion of the eye. For example, only the optical path and surrounding region might be imaged.

Figure 4B:
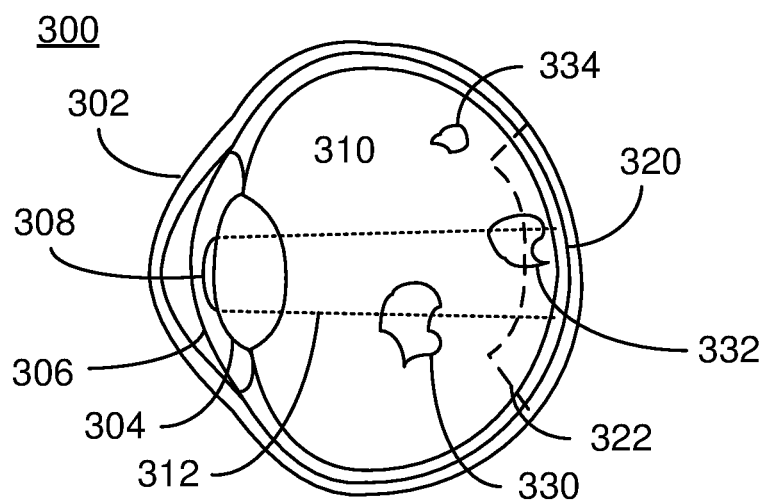

Keep out zones are determined by the ophthalmic laser apparatus based on the image data and any additional data for the patient, via step 154. Step 154 is analogous to step 104. Step 154 may thus include identifying structures such as the retina 320 and setting a keep out zone to be the structure and a region within a particular distance of the structure. The physician may be allowed to adjust the size and/or location of the keep out zone 322 as part of step 154. For example, the keep out zone 322 might be made thinner such that a region a smaller distance from the retina 320 is included. However, there may also be a minimum distance beyond which the physician is not allowed to change the size or position of the keep out zone. For example, the keep out zone may be required to include the portion of the retina 320 already within the keep out zone and a region within some small distance of this portion of the retina 320. FIG. 4B depicts the information added in step 154. Thus, the optical path 312 is indicated by dotted lines. In addition, a keep out zone 322 indicated by dashed lines has also been determined. The keep out zone 322 includes a portion of the retina 320 in and around the optical path 312 and a region a particular distance anterior of the retina 320. Other keep out zones (not shown in FIG. 4B for simplicity) may be provided in step 154.

The vitreous opacities are identified by the data processing unit 230 based on the image data, via step 156. Step 156 may also utilize information in the data store 250. Step 156 is thus analogous to step 106. Thus, the vitreous opacities 330, 332 and 334 are defined in step 156. In some embodiments, the vitreous opacity 334 might be omitted from the vitreous opacities determined in step 156 because the vitreous opacity may be sufficiently small and/or sufficiently far from the optical path 312 to be considered by the method 150. However, in other embodiments, the vitreous opacity 334 is included. Step 156 may also include ranking the vitreous opacities 330, 332 and 334 based on size, location and density. The ranking is presumed to be, in order, 332, 334 and 336.

One of the vitreous opacities 330, 332, 334 is selected by the data processing unit 230 for removal, via step 158. Step 158 is analogous to step 108. In the embodiment shown, the vitreous opacity 330 is selected for removal because it was ranked first in step 156. In embodiments in which the ranking is not performed as part of step 156, the ranking may be performed as part of step 158.

A confirmation for removal of the undesirable feature is received by the data processing unit 230, via step 160. Step 160 is analogous to step 110 optional. Step 140 may include receiving input from a physician via the U/I 240, response. If no confirmation is received, then the method may return to step 152 or the physician may be allowed to select a different undesirable feature for removal via the U/I.

Figure 4C:
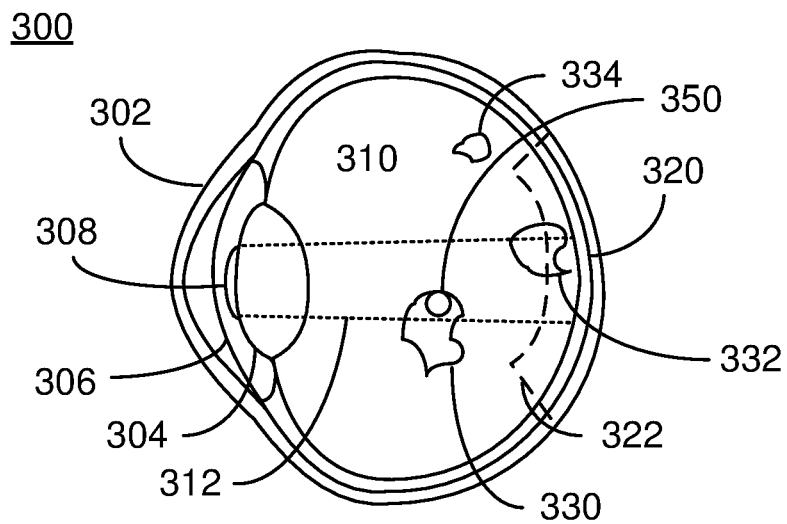

In response to receiving the confirmation, the laser 212 is controlled by the controller 210 to automatically performed removal of at least part of the vitreous opacity 330. In order to do so, steps 162, 163, 164, 166, 168 and 170 may be used. For example, the controller 220 automatically aims the laser 210 at location(s) within the selected vitreous opacity 330 and outside of the keep out ozone 222, via step 162. If a sufficient amount of the vitreous opacity 330 selected for removal were in the keep out zone 322, then the physician may be allowed to override the method 150 and focus the laser 210 within the keep out zone 322, via step 163. FIG. 4C depicts the image 300 with the laser aimed at target 350. This target 350 is within the selected vitreous opacity 330 and outside of the keep out zone 322. Further, the target 350 is within the optical path 312, which may be desirable. As a result, the portion of the vitreous opacity 330 within the optical path 312 and more likely to affect vision may be removed first.

Once aimed, the laser 210 may be fired using the controller 220 to turn the laser 210 on and off, via step 164. As a result, at least a portion of the selected vitreous opacity 330 is vaporized.

Figure 4D:
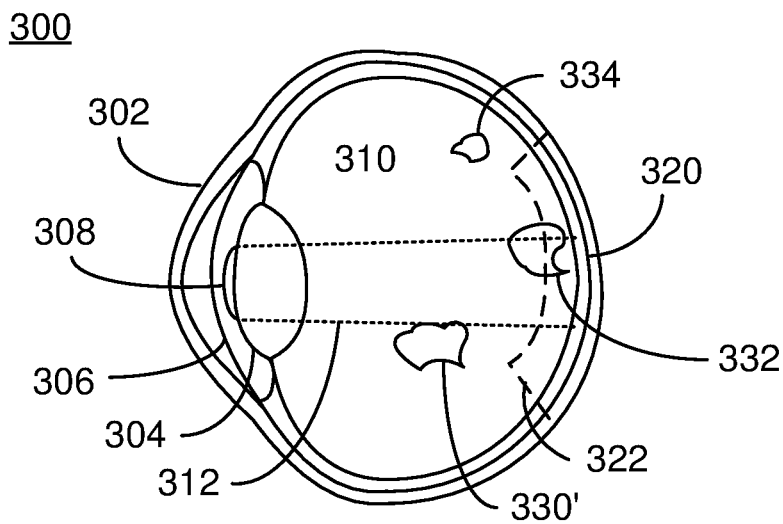

The eye is optionally reimaged, via step 166. Step 166 is analogous to step 152. FIG. 4D depicts the image 300 of the eye after step 166 is performed. Thus, the vitreous opacity 330' is smaller, has changed shape and may have moved. It is determined whether the remaining portion of the selected vitreous opacity 330' may be tracked. Tracking may include comparing the image(s) of the eye taken after the laser energy is applied in step 164 with those taken in step 152 and matching the size, location, shape and/or other features of the vitreous opacities. As can be seen in FIGS. 4B and 4D, the vitreous opacity 330' corresponds to the vitreous opacity 330 and is still sufficiently large for tracking. The selected vitreous opacity 330' is thus tracked in step 170. Stated differently, the shape and location of the vitreous opacity 330' may be saved. Step 162 may then be returned to. Steps 162, 164, 166, 168 and 170 may be iteratively performed until the vitreous opacity 330' may no longer be tracked.

Figure 4E:
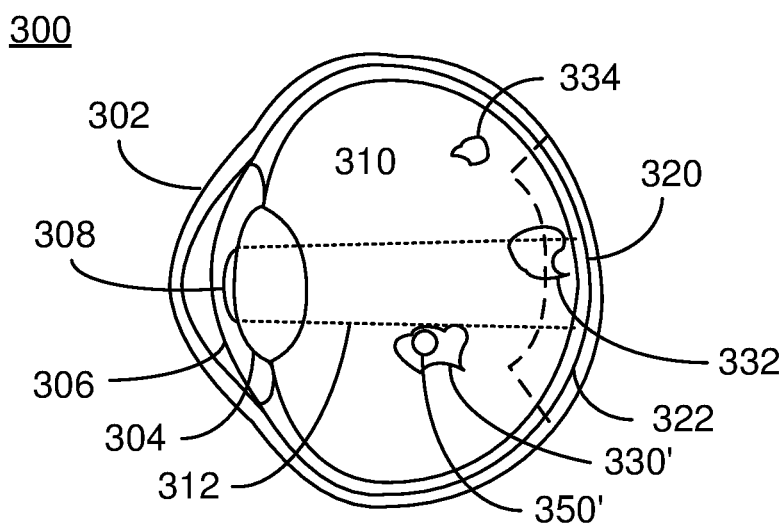
Figure 4F:
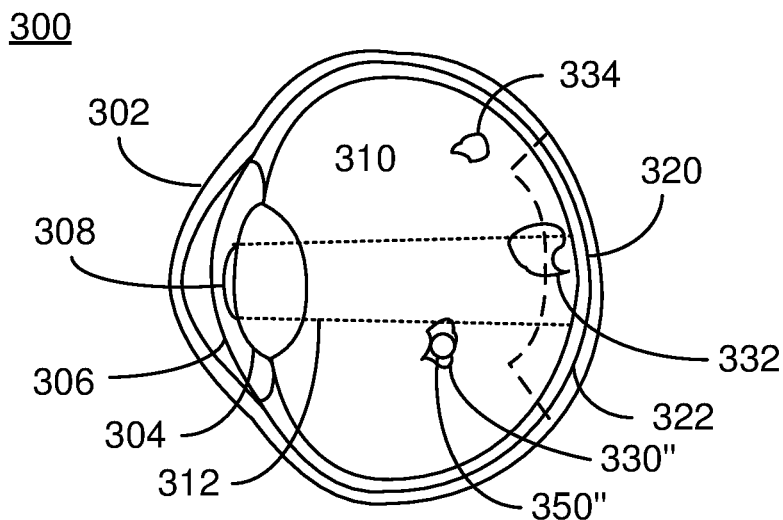
Figure 4G:
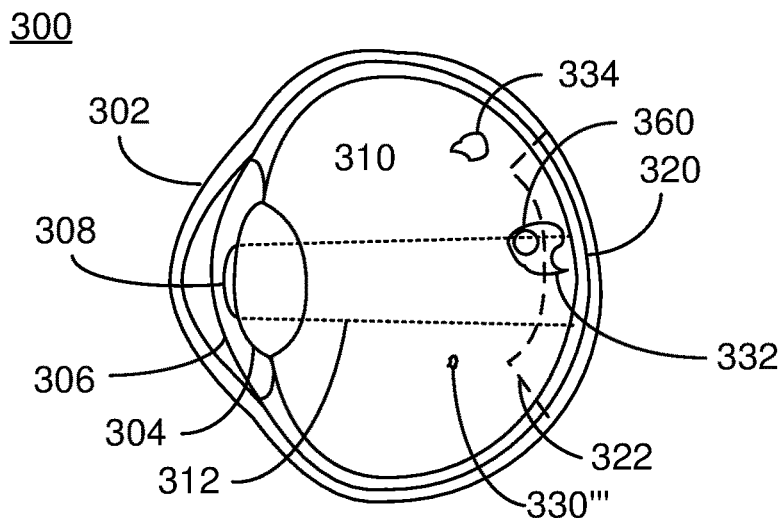

Thus, FIG. 4E depicts the target 350' for the vitreous opacity 330' determined on the next (second) iteration of step 162. FIG. 4F depicts the target 350'' on the third iteration of the method 150. Thus, the vitreous opacity 330'' is even smaller. The target 350'' is both at least partially within the vitreous opacity 330'' and outside of the keep away zone 322. FIG. 4G depicts the image after the vitreous opacity 330''' after the third iteration of the fining of the laser in step 164. The vitreous opacity 330''' can no longer be tracked. Thus, the vitreous opacity 330''' may be considered removed.

Because it is determined in step 168 after three iterations that the vitreous opacity 330''' can no longer be tracked, it is determined in step 172 whether there may be additional vitreous opacities to be removed. As can be seen in FIG. 4G, vitreous opacities 332 and 334 remain. Thus, step 154 is returned to using the image data from step 166. Alternatively, step 152 may be returned to in order to obtain more image data.

Figure 4H:
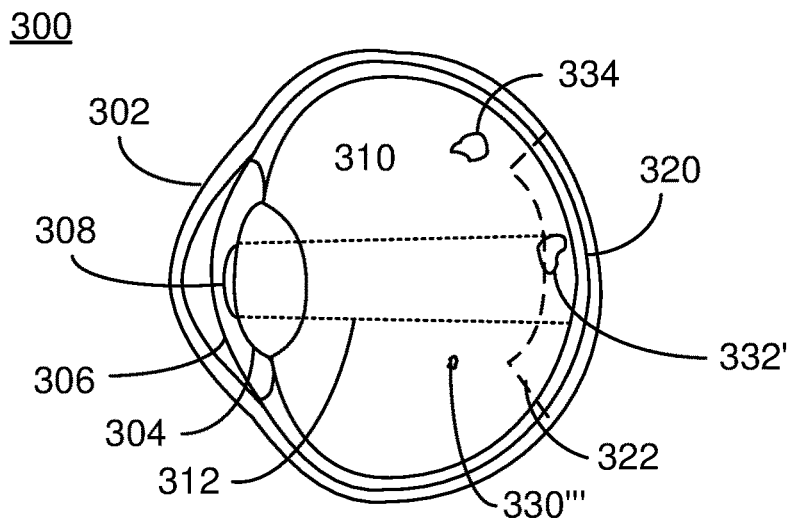
Figure 4I:
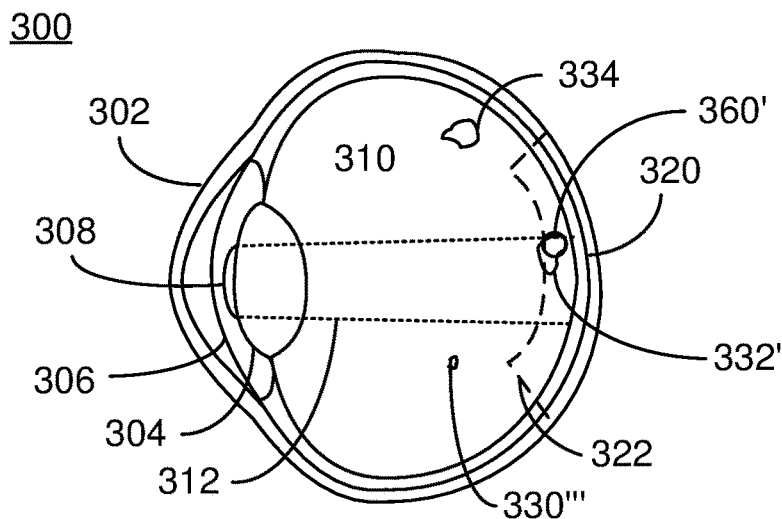
Figure 4J:
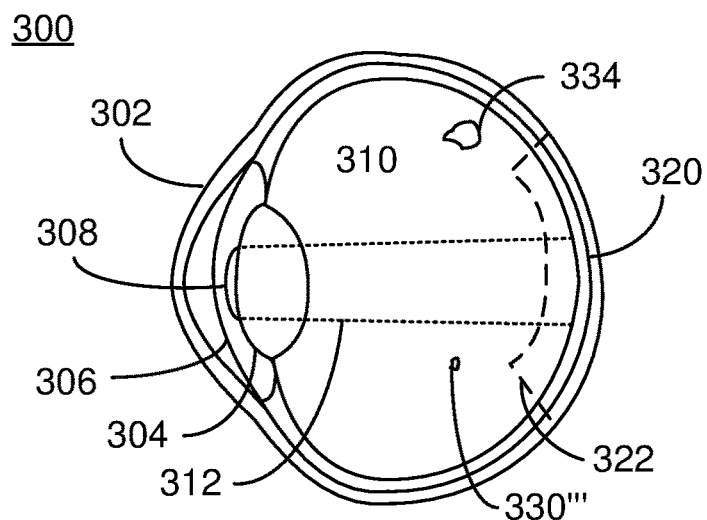

Thus, steps 154 through 172 may be repeated. As can be seen in FIG. 4G, the next vitreous opacity 332 is targeted in step 162. The target 360 for the vitreous opacity 443 is both within the vitreous opacity 332 and outside of the keep out zone 322. FIG. 4H depicts the image after step 164 is performed for the vitreous opacity 332. Thus, only a portion of the vitreous opacity 332' remains. However, substantially all of the vitreous opacity 332' is in the keep out zone 322. In some embodiments, this would complete removal of the vitreous opacity 332'. However, FIG. 4I depicts a target 360' on the vitreous opacity 332' and within the keep out zone 320. This is because the physician has used step 163 to override the requirement that the laser 210 be focused outside of the keep out zone 322. The laser 210 is fired by the controller 220 in step 164. FIG. 4J depicts an image of the eye taken in step 166. Thus, the vitreous opacity 332' has been completely removed.

Figure 4K:
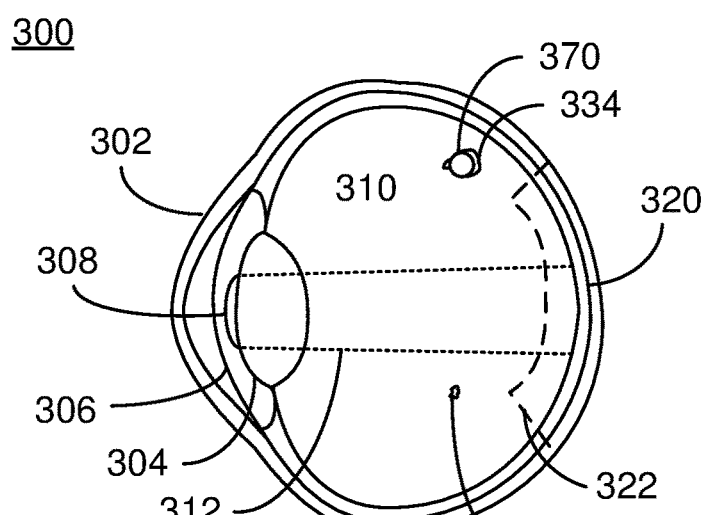

In some embodiments, this might complete the method 150 because vitreous opacities within the optical path 312 have been removed. However, in this case, removal of the remaining identified and trackable vitreous opacity 334 is desired. Thus, the method 150 repeats and the physician confirms removal of vitreous opacity 334 in the next iteration of step 160. FIG. 4K depicts the image 300 after the controller aims the laser in step 152. Thus, target 370 is shown. The target 370 for the laser 210 is within the vitreous opacity 334 and outside of the keep out zone 322. The laser 210 may then be fired in step 164. The steps 162, 163, 164, 166, 168 and 170 may be repeated until the vitreous opacity 334 is not trackable and removed.

Figure 4L:
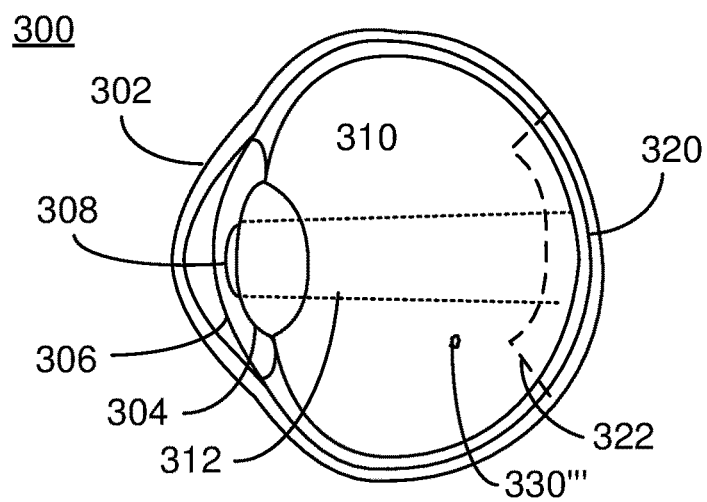

FIG. 4L depicts an image of the eye after removal of the vitreous opacity 334. The image 300 may be captured after the last iteration of step 166 for the vitreous opacity 334. Thus, step 168 determines that the opacity (not present in FIG. 4L) is not trackable. Step 172 may also determine that there are not more vitreous opacities. This is because the opacity 330'' may be sufficiently small that it does not meet any of the thresholds set for localizing opacities. Thus, the method 150 completes.

Using the method 150, a physician may be able to more quickly and easily remove vitreous floaters, from the eye. Instead of viewing the eye, manually aiming the laser and turning the laser on or off, the physician may simply confirm removal in step 160 and optionally change or override keep out zones in steps 154 and/or 163. The system 200 may perform some or all of the method 150. Thus, the burden on the physician may be reduced and the time taken to remove each floater may be greatly reduced. Consequently, the burden on both the physician and patient may be diminished. The method 150 may be safer for the patient. Further, the method 150 may be performed non-invasively. Consequently, the removal of undesirable features via a laser may be improved.

A method and system for assisting a physician in non-invasively removing undesirable features in an eye have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

I claim:

1. A system for performing an ophthalmic procedure on an eye including a lens and a retina, the eye having an optical path from the lens to the retina, the system comprising:
    a laser;
    a data processing unit operable to:
        receive an image of at least a portion of the eye;
        determine at least one keep out zone based on the image, the at least one keep out zone including the retina;
        identify at least one undesirable feature based on the image;
        select an undesirable feature of the at least one undesirable feature for removal, at least a portion of the undesirable feature residing outside of the at least one keep out zone;
        allow a user to change a size of a keep out zone of the at least one keep out zone, wherein allowing the user to change the size of the keep out zone comprises preventing the user from resizing the keep out zone such that the keep out zone is smaller than the retina;
    a control unit coupled with the laser and the data processing unit, the control unit operable to control the laser to perform laser removal of the at least the portion of the undesirable feature without targeting any portion of the at least one keep out zone.

2. The system of claim 1 wherein the at least one undesirable feature is at least one vitreous opacity.

3. The system of claim 1 wherein the control unit is further operable to set a target of the laser within the at least the portion of the undesirable feature and fires the laser such that the target is within the at least the portion of the undesirable feature.

4. The system of claim 3 wherein the data processing unit is further operable to track a remaining portion of the undesirable feature in response to the laser being fired.

5. The system of claim 1, further comprising an imaging system coupled with the control unit and the data processing unit, the imaging system operable to capture the image.

6. The system of claim 1, wherein identifying the at least one undesirable feature comprises identifying an undesirable feature with an opacity greater than an opacity threshold.

7. The system of claim 1, wherein identifying the at least one undesirable feature comprises identifying an undesirable feature with a size greater than a size threshold.

8. The system of claim 6, wherein identifying the at least one undesirable feature further comprises identifying an undesirable feature with a size greater than a size threshold.

9. The system of claim 6, wherein the opacity threshold is user provided.

10. The system of claim 7, wherein the size threshold is user provided.

11. The system of claim 1, wherein the at least one undesirable feature comprises at least two undesirable features, and wherein selecting the undesirable feature of the at least one undesirable feature for removal comprises ranking the at least two undesirable features based on size, location, density or shape.

12. The system of claim 11, wherein selecting the undesirable feature of the at least one undesirable feature for removal further comprises selecting the highest ranked undesirable feature of the at least two undesirable features for removal.

13. The system of claim 1, wherein performing laser removal by the control unit comprises setting a laser power or laser application time based on a location targeted.

14. The system of claim 13, wherein performing laser removal by the control unit further comprises using a lower laser energy or shorter laser application time for locations targeted closer to a keep out zone than locations targeted further away from the keep out zone.

* * * * *